(12) United States Patent
Lagwinski et al.

(10) Patent No.: US 7,384,795 B2
(45) Date of Patent: Jun. 10, 2008

(54) METHODS FOR VERIFYING FLUID MOVEMENT

(75) Inventors: Willy Lagwinski, Walnut Creek, CA (US); Charles A. Harrington, Castro Valley, CA (US); Bruce H. Phelps, Clayton, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 620 days.

(21) Appl. No.: 10/655,588

(22) Filed: Sep. 5, 2003

(65) Prior Publication Data

US 2004/0197929 A1 Oct. 7, 2004

Related U.S. Application Data (60) Provisional application No. 60/408,296, filed on Sep. 6, 2002.

(51) Int. Cl.
| | |
|---|---|
| *G01N 1/10* | (2006.01) |
| *G01N 35/00* | (2006.01) |
| *G01N 35/08* | (2006.01) |
| *G01N 1/00* | (2006.01) |
| *G01N 21/77* | (2006.01) |

(52) U.S. Cl. .................. 436/180; 422/50; 422/68.1; 422/81; 422/82; 422/82.05; 422/82.07; 422/82.08; 436/43; 436/53; 436/174; 436/179; 977/700; 977/852; 977/962; 977/901; 977/841

(58) Field of Classification Search .................. 422/50, 422/68.1, 81, 82, 82.05, 82.07, 82.08; 436/43, 436/53, 174, 179, 180; 977/700, 852, 962, 977/901, 841

See application file for complete search history.

(56) References Cited

U.S. PATENT DOCUMENTS

| | | | |
|---|---|---|---|
| 5,120,661 | A | 6/1992 | Baker et al. |
| 5,262,357 | A | 11/1993 | Alivisatos et al. |
| 5,504,014 | A | 4/1996 | Lindsey et al. |
| 5,505,928 | A | 4/1996 | Alivisatos et al. |
| 5,525,377 | A | 6/1996 | Gallagher et al. |
| 5,537,000 | A | 7/1996 | Alivisatos et al. |
| 5,571,018 | A | 11/1996 | Fitzgerald |
| 5,990,479 | A | 11/1999 | Weiss et al. |
| 6,037,180 | A | 3/2000 | Yorkgitis et al. |

(Continued)

FOREIGN PATENT DOCUMENTS

EP 0703451 3/1996

(Continued)

OTHER PUBLICATIONS

Murray et al., "Synthesis and Characterization of nearly Monodisperse CdE (E=S, Se, Te) Semiconductor Nanocrystallites," J. Am. Chem. Soc., vol. 115, pp. 8706-8715 (1993).

(Continued)

*Primary Examiner*—Brian Sines
(74) *Attorney, Agent, or Firm*—Alisa A. Harbin; Joseph P. Meara (57) ABSTRACT

Methods for using semiconductor nanocrystals for determining fluid movement, fluid dilution and fluid removal are described. Methods for using semiconductor nanocrystals for monitoring and quantifying the amounts of solid materials dissolved in a liquid are also described.

16 Claims, 1 Drawing Sheet

U.S. PATENT DOCUMENTS

| | | | |
|---|---|---|---|
| 6,048,616 | A | 4/2000 | Gallagher et al. |
| 6,114,038 | A | 9/2000 | Castro et al. |
| 6,179,912 | B1 | 1/2001 | Barbera-Guillem et al. |
| 6,207,229 | B1 | 3/2001 | Bawendi et al. |
| 6,207,392 | B1 * | 3/2001 | Weiss et al. .................. 435/7.1 |
| 6,221,602 | B1 | 4/2001 | Barbera-Guillem et al. |
| 6,225,198 | B1 | 5/2001 | Alivisatos et al. |
| 6,235,540 | B1 | 5/2001 | Siman et al. |
| 6,261,779 | B1 | 7/2001 | Barbera-Guillem et al. |
| 6,274,323 | B1 | 8/2001 | Bruchez et al. |
| 6,306,610 | B1 | 10/2001 | Bawendi et al. |
| 6,306,736 | B1 | 10/2001 | Alivisatos et al. |
| 6,309,701 | B1 | 10/2001 | Barbera-Guillem |
| 6,319,426 | B1 | 11/2001 | Bawendi et al. |
| 6,319,607 | B1 | 11/2001 | Barbera-Guillem et al. |
| 6,322,901 | B1 | 11/2001 | Bawendi et al. |
| 6,326,144 | B1 | 12/2001 | Bawendi et al. |
| 6,333,110 | B1 | 12/2001 | Barbera-Guillem |
| 6,423,551 | B1 | 7/2002 | Weiss et al. |
| 6,426,513 | B1 | 7/2002 | Bawendi et al. |
| 6,617,583 | B1 * | 9/2003 | Bawendi et al. ........ 250/370.01 |
| 6,630,307 | B2 * | 10/2003 | Bruchez et al. ................. 435/6 |
| 6,774,361 | B2 * | 8/2004 | Bawendi et al. ............ 250/307 |
| 2001/0023078 | A1 | 9/2001 | Bawendi |
| 2001/0034034 | A1 | 10/2001 | Bruchez |
| 2001/0055764 | A1 | 12/2001 | Empedocles |
| 2003/0213503 | A1 | 11/2003 | Price et al. |

FOREIGN PATENT DOCUMENTS

| | | |
|---|---|---|
| EP | 0959140 | 11/1999 |
| WO | WO 99/26299 | 5/1999 |

OTHER PUBLICATIONS

Peng et al., "Epitaxial Growth of Highly Luminescent CdSe/CdS Core/Shell Nanocrystals with Photostability and Electronic Accessibility," J. Am. Chem. Soc., vol. 119, pp. 7019-7029 (1997).

Dabbousi et al., "(CdSe)ZnS Core-Shell Quantum Dots: Synthesis and Characterization of a Size Series of Highly Luminescent Nanocrystallites," J. Phys. Chem. B, vol. 101, pp. 9463-9475 (1997).

S. J. Rosenthal, "Bar-coding Biomolecules with Fluorescent Nanocrystals," Nature Biotechnology, vol. 19, pp. 621-622 (2001).

Peng et al., "Shape Control of CdSe nanocrystals," Nature, vol. 404, pp. 59-61 (2000).

Bruchez Jr. et al., "Semiconductor Nanocrystals as Fluorescent Biological Labels," Science, vol. 281, pp. 2013-2016 (1998).

Gerion et al., "Sorting Fluorescent Nanocrystals with DNA," J. Am. Chem. Soc., vol. 124, pp. 7070-7074 (2002).

Han et al., "quantum-dot-tagged Microbeads for Multiplexed Optical Coding of Biomolecules," Nature Biotechnology, vol. 19, pp. 631-635s (2001).

Henry, CM "Bar Coding Biomolecules/Quantum-Dot-Tagged Polymeric Microbeads Provide Multiplexed Optical Coding" Chemical and Engineering News, ACS Washington DC vol. 79, No. 29.

* cited by examiner

METHODS FOR VERIFYING FLUID MOVEMENT

In accordance with 35 U.S.C. §119 (e), the benefit of provisional application No. 60/408,296 filed Sep. 6, 2002, is hereby claimed. The entire contents of this provisional application are incorporated herein by reference.

BACKGROUND OF THE INVENTION

The present invention relates generally to the use of fluorescent tracers to determine, analyze and quantify fluid movement, fluid dilution and fluid removal. Specifically, the invention relates to the use of quantum-sized particles to determine, analyze and quantify fluid movement, fluid dilution and fluid removal. The present invention further relates to methods for monitoring and quantifying the amounts of solid materials dissolved in a liquid.

Quantum-sized particles, i.e., those having diameters within the range of about 0.1 nm to about 50 nm, also known as quantum dots or nanocrystals, are known for the luminescent properties that they possess due to their small size, large surface area and optico-electronic properties. Luminescent nanocrystals have been shown to be useful as detectable labels for applications such as oligonucleotide tags, tissue imaging stains, protein expression probes, and in the detection of biological compounds both in vitro and in vivo.

Typically the transfer of fluid was determined by employing an organic dye or measuring the flow of fluid past an injector. One drawback of organic dyes is the deterioration of fluorescence intensity upon prolonged and/or repeated exposure to excitation light. This fading, called photobleaching, is dependent on the intensity of the excitation light and the duration of the illumination. In addition, conversion of the dye into a non-fluorescent species is irreversible. Furthermore, the degradation products of dyes are organic compounds which may interfere with the composition being examined. Moreover, at high concentrations organic dyes self absorb, limiting their linear dynamic range.

Another drawback of organic dyes is a spectral overlap which exists from one dye to another. This is due in part to the relatively wide emission spectra of organic dyes and the overlap of the spectra near the tailing region. In addition, low molecular weight dyes may be impractical for some applications because they do not provide a bright enough fluorescent signal. The ideal fluorescent label should fulfill many requirements. Among the desired qualities are the following: (i) high fluorescent intensity (for detection in small quantities), (ii) a separation of at least 50 nm between the absorption and fluorescing frequencies, (iii) solubility in the test composition, (iv) stability towards harsh conditions and high temperatures, (v) a symmetric emission lineshape for easy analysis, (vi) uniform dispersion in the test composition; (vii) compatibility with automated analysis; (viii) inherently large dynamic range with minimal self quenching; and (ix) being chemically inert with respect to the active components making up the fluid being monitored.

The differences in the chemical properties of standard organic fluorescent dyes make multiple, parallel assays quite impractical since different chemical reactions may be involved for each dye used in the variety of applications of fluorescent labels. Furthermore, the differences in the chemical properties of standard organic fluorescent dyes make multiple, parallel assays impractical as different chemical reactions may be involved for each dye used in the variety of applications of fluorescent labels.

Moreover, there are chemical and physical limitations to the use of organic fluorescent dyes. One of these limitations is the variation of excitation wavelengths of different colored dyes. As a result, simultaneously using two or more fluorescent tags with different excitation wavelengths requires multiple excitation light sources. This requirement thus adds to the cost and complexity of methods utilizing multiple fluorescent dyes. Moreover, organic dyes exhibit quenching of fluorescence at even moderate concentrations, leading to significant non-linear dilution effects.

A drawback of measuring the flow of fluid past through an injector is that this method is not capable of verifying that the fluid has actually been delivered to the desired device or receptacle.

Thus, there is a need in the art for a fluorescent label that satisfies the above-described criteria for use in systems where one or more fluids are transferred and which is able to verify and quantify the addition of fluid to a reactor vessel or the like.

SUMMARY OF THE INVENTION

It is an object of the present invention to overcome the drawbacks of the prior art. Luminescent semiconductor nanocrystals offer several advantages over conventional organic dyes. Semiconductor nanocrystals typically have higher absorption cross sections than comparable organic dyes, higher quantum yields, better chemical and photochemical stability, and narrower and more symmetric emission spectra. Furthermore, the absorption and emission properties vary with the particle size and composition. and, thus, can be systematically tailored. Finally, semiconductor nanocrystals can be used to independently quantify the amount of fluid transferred or diluted with a degree of certainty.

A variety of methods have been reported for the preparation of semiconductor nanocrystals. These methods include inverse micelle preparations, arrested precipitation, aerosol processes, pot-stirring processes, and sol-gel processes. Control of the properties of nanocrystals by the application of coatings or shells has been reported, notably in International Patent Publication No. WO 99/26299 (PCT/US98/23984), "Highly Luminescent Color-Selective Materials," Massachusetts Institute of Technology, applicant, which was published on May 27, 1999, and references cited therein. The application of an inorganic shell, for example, can increase the quantum yield of the nanocrystal as well its chemical stability and photostability. The techniques for applying a shell are stirred-pot techniques that are usually similar to those used for the preparation of the core. Like the diameter of the core, the thickness of the shell affects the properties of the finished product, and the thickness may vary with the same system parameters that affect the core. The difficulties in controlling these parameters in a stirred-pot system lead to difficulties in controlling the nature and quality of the final product.

The present invention is also based on the discovery that semiconductor nanocrystals can be used as reliable and sensitive detectable labels in a variety of biological and chemical applications. Semiconductor nanocrystals (also know as quantum dot and Qdot™ nanocrystals) can be produced having characteristic spectral emissions. These spectral emissions can be tuned to a desired energy by varying the particle size, size distribution and/or composition of the particle. The location of the semiconductor nanocrystal can be determined, for example, by irradiation of the sample with an energy source, such as an excitation light source. The semiconductor nanocrystal emits a characteristic emission spectrum which can be observed and measured, for example, spectroscopically.

Emission spectra of a population of semiconductor nanocrystals can be manipulated to have linewidths as narrow as 25-30 nm, depending on the size distribution heterogeneity of the sample population. Accordingly, the use of semiconductor nanocrystals allows for detection and quantification of one, or even several, different biological or chemical moieties in a single application. The combination of tunability, narrow linewidths, and symmetric emission spectra provides for high resolution of multiply sized nanocrystals, e.g., populations of monodisperse semiconductor nanocrystals having multiple distinct size distributions within a system, and simultaneous detection and/or quantification of a variety of chemical or biological components.

In addition, the range of excitation wavelengths of the nanocrystals is broad and can be higher in energy than the emission wavelengths of all available semiconductor nanocrystals. Consequently, this allows the use of a single energy source, such as light, usually in the ultraviolet or blue region of the spectrum, to effect simultaneous excitation of all populations of semiconductor nanocrystals in a system having distinct emission spectra. Semiconductor nanocrystals are also more robust than conventional organic fluorescent dyes and are more resistant to photobleaching than the organic dyes. The robustness of the nanocrystal also alleviates the problem of contamination of degradation products of the organic dyes in the system being examined. Therefore, the present invention provides a uniquely valuable method for monitoring the addition and/or quantifying the amounts of components being mixed together in a chemical or biological system.

The present invention further relates to methods for monitoring and quantifying the amounts of solid materials dissolved in a liquid. Many chemical and biological materials are purified as aqueous solutions or when dissolved in a variety of organic solvents. Through a series of manipulations of these solutions, such as, for example, chromatography, electroporetic separations, elutions, dialysis, and the like, the target component is separated from contaminants and obtained as a purified material in solution. Chemically inert semiconductor nanocrystals can be homogeneously dispersed at a known concentration into the purified fluid. After lyophilization, the semiconductor nanocrystals would remain homogeneously dispersed in the solid product and could serve as a tracer for the amount of the solid added to make the second composition. This would be particularly useful for primary standards that are frequently provided as lyophilized materials (for stability reasons) and would provide improved precision when preparing the initial stock solutions as well when preparing the subsequent dilutions.

According to one aspect of the invention, there has been provided a method for verifying the transfer of a fluid from a first composition to a second composition comprising: providing a first composition having a first fluid therein; providing a second composition having a second fluid therein, wherein said second composition includes a predetermined amount of homogeneously dispersed luminescent semiconductor nanocrystals capable of emitting electromagnetic radiation in a narrow wavelength band when excited; transferring all or a portion of said second composition into said first composition to form a third composition; exposing said third composition to energy capable of exciting said luminescent semiconductor nanocrystals; and detecting the electromagnetic radiation emitted from said luminescent semiconductor nanocrystals in said third composition. It should be understood that in the present invention it is contemplated that the first fluid may be a liquid, gas, or even a vacuum.

According to another aspect of the invention, there has been provided a method for verifying the transfer of a fluid from a first composition to a second composition which further includes quantifying the luminescent semiconductor nanocrystals in said third composition to verify the delivery amount of said second composition into said first composition to form said third composition. The delivery amount is verified by determining the relative fluorescence of the luminescent semiconductor nanocrystals in the third composition. While the present invention has been described as verifying the amount of the luminescent semiconductor nanocrystals present in the second composition, it should be understood that the present invention also contemplates that the luminescent semiconductor nanocrystals are present in the first composition with the second composition being added thereto to form the third composition.

According to another aspect of the invention, there is provided a method for verifying the transfer of a fluid from a first composition to a second composition where the semiconductor nanocrystal is a core/shell nanocrystal. In another aspect of the invention, the semiconductor nanocrystal has a diameter between about 2 nm and about 50 nm, preferably between about 2 nm and about 20 nm. In yet another aspect of the invention, the semiconductor nanocrystal is selected from the group consisting of ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and mixtures thereof. Preferably the semiconductor nanocrystal has a core which comprises CdSe and a shell which comprises CdS or ZnS. Another aspect of the invention is that the semiconductor nanocrystal has a core diameter between about 2 nm and about 50 nm, preferably between about 2 nm and 6 nm and the shell has a thickness of about 2 nm. The method may include nucleic acid testing.

According to another aspect of the invention, there is provided a method for verifying the transfer of a fluid from a first composition to a second composition where the semiconductor nanocrystals are monodisperse. In another aspect of the invention, the semiconductor nanocrystal is linked to the components present in said second fluid. In another aspect of the invention, the semiconductor nanocrystals are homogeneously dispersed in said second fluid.

According to another aspect of the invention, there is provided a method for monitoring the flow of a reagent comprising: providing a reagent being admixed with a predetermined amount of luminescent semiconductor nanocrystals capable of emitting electromagnetic radiation in a narrow wavelength band when excited; transferring all or a portion of said reagent to a reaction vessel; exposing said reaction vessel to energy capable of exciting said luminescent semiconductor nanocrystals; and detecting the electromagnetic radiation emitted from said luminescent semiconductor nanocrystals.

According to another aspect of the invention, there is provided a method for monitoring the flow of a reagent which further includes quantifying the luminescent semiconductor nanocrystals in said reaction vessel to verify the delivery quantity of said reagent.

According to another aspect of the invention, there is provided a method for monitoring the flow of a reagent comprising: providing a reagent admixed with a predetermined amount of luminescent semiconductor nanocrystals capable of emitting electromagnetic radiation in a narrow wavelength band when excited; transferring all or a portion of said reagent to a reaction vessel; obtaining a unit sample from said reaction vessel; exposing said sample to energy capable of exciting said luminescent semiconductor nanocrystals; detecting the electromagnetic radiation emitted from said luminescent semiconductor nanocrystals in said sample to verify the delivery of said reagent.

According to another aspect of the invention, there is provided a method for monitoring the flow of a reagent further comprising quantifying the luminescent semiconductor nanocrystals in said sample to verify the amount of reagent delivered to said reaction vessel.

According to another aspect of the invention, there is provided a method for verifying the transfer of a plurality of fluids to a container, comprising: providing a plurality of compositions having fluid therein wherein each individual composition includes a predetermined amount of different luminescent semiconductor nanocrystals capable of emitting electromagnetic radiation at different wavelength bands corresponding to each of said luminescent semiconductor nanocrystals when excited; transferring all or a portion of said plurality of fluids into said container; exposing said container to energy capable of exciting said plurality of luminescent semiconductor nanocrystals; and detecting the electromagnetic radiation emitted from said plurality of luminescent semiconductor nanocrystals to determine the transfer of said plurality of fluids. In another embodiment, the container may be a reaction vessel.

According to another aspect of the invention, there is provided a method for verifying the transfer of a plurality of fluids to a reaction vessel which further includes quantifying the luminescent semiconductor nanocrystals to verify the delivery amount of said plurality of compositions into said reaction vessel.

According to another aspect of the invention, there is provided a method for verifying the transfer of a plurality of fluids to a container wherein said plurality of compositions is transferred into said container in a batchwise transfer or a sequential transfer. The fluids may be selected from the group consisting of reagents, buffers, solvents, and the like and the container may be, for example, a reaction vessel.

According to another aspect of the invention, there is provided a method for preparing a dilute solution, comprising: providing a first solution having a predetermined concentration of luminescent semiconductor nanocrystals capable of emitting electromagnetic radiation in a narrow wavelength band when excited; diluting said first solution with a second solution to a predetermined dilution ratio; and verifying said predetermined dilution ratio by exposing said diluted solution to energy capable of exciting said luminescent semiconductor nanocrystals and detecting the electromagnetic radiation emitted from said plurality of luminescent semiconductor nanocrystals and comparing the relative fluorescence to the expected amount of fluorescence to verify the predetermined dilution ratio. It should be understood that the first solution may include, for example, an active ingredient and the second solution may be, for example, an acceptable diluent.

According to another aspect of the invention, there is provided a method for determining the cleanliness of a container, comprising:
  providing a container having a plurality of components therein;
  adding to said container luminescent semiconductor nanocrystals capable of emitting electromagnetic radiation in a narrow wavelength band when excited; removing the contents from said container upon completion of the reaction; cleaning said container; exposing said container to energy capable of exciting said luminescent semiconductor nanocrystals and detecting the electromagnetic radiation emitted from said plurality of luminescent semiconductor nanocrystals to verify the presence of residual components from said reaction; and determining the relative quantity of said luminescent semiconductor nanocrystals remaining in said reaction vessel. The components may be any chemical or biological species or adjuvant capable or being reacted or transformed.

According to another aspect of the invention, there is provided a method for determining the cleanliness of a container wherein the container is a reaction vessel such as, for example, a bioreactor or a fermentor. Another aspect of the invention includes iterative cleaning of said reaction vessel until the quantity of said luminescent semiconductor crystals is below a predetermined level.

DETAILED DESCRIPTION OF THE PREFERRED EMBODIMENTS

The practice of the present invention will employ, unless otherwise indicated, conventional techniques of synthetic organic chemistry, biochemistry, molecular biology, and the like, which are within the skill of the art. Such techniques are explained fully in the literature. See, e.g., Kirk-Othmer's Encyclopedia of Chemical Technology; House's Modern Synthetic Reactions; the Marvel et al. text ORGANIC SYNTHESIS; Collective Volume 1, and the like.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

In describing the present invention, the following terms will be employed, and are intended to be defined as indicated below.

The terms "semiconductor nanocrystal" and "quantum dot" are used interchangeably herein and refer to an inorganic crystallite between about 1 nm and about 1000 nm in diameter or any integer or fraction of an integer therebetween, preferably between about 2 nm and about 50 nm or any integer or fraction of an integer therebetween, more preferably about 2 nm to about 20 nm (such as about 2, 3, 4, 5, 6, 7, 8, 9, 10, 11, 12, 13, 14, 15, 16, 17, 18, 19, or 20 nm).

A semiconductor nanocrystal is capable of emitting electromagnetic radiation upon excitation (i.e., the semiconductor nanocrystal is luminescent) and includes a "core" of one or more first semiconductor materials, and may be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the group II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, and an alloy or a mixture thereof.

A semiconductor nanocrystal is, optionally, surrounded by a "coat" of an organic capping agent. The organic capping agent may be any number of materials, but has an affinity for the semiconductor nanocrystal surface. In general, the capping agent can be an isolated organic molecule, a polymer (or a monomer for a polymerization reaction), an inorganic complex, and an extended crystalline structure. The coat is used to convey solubility, e.g., the ability to disperse a coated semiconductor nanocrystal homogeneously into a chosen solvent, functionality, binding properties, or the like. In addition, the coat can be used to tailor the optical properties of the semiconductor nanocrystal. Methods for producing capped semiconductor nanocrystals are discussed below and is known to those of ordinary skill in the art.

By "luminescence" is meant the process of emitting electromagnetic radiation (light) from an object. Luminescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

"Monodisperse particles" include a population of particles wherein at least about 60% of the particles in the population, preferably about 75% to 90% of the particles in the population, more preferably about 80% to 95% of the particles in the population, most preferably about 90% to 95% of the particles in the population, or any integer in between this range, fall within a specified particle size range. A population of monodispersed particles deviate less than 10% rms (root-mean-square) in diameter and preferably less than 5% rms. Monodisperse semiconductor nanocrystals have been described in detail in Murray et al. (J. Am. Chem. Soc., 115:8706 (1993)); and in the thesis of Christopher Murray, "Synthesis and Characterization of II-VI Quantum Dots and Their Assembly into 3-D Quantum Dot Superlattices", Massachusetts Institute of Technology, September, 1995, which are herein incorporated by reference.

By use of the term "a narrow wavelength band" or "narrow spectral linewidth" with regard to the electromagnetic radiation emission of the semiconductor nanocrystal is meant a wavelength band of emissions not exceeding about 40 nm, and preferably not exceeding about 20 nm in width and symmetric about the center, in contrast to the emission bandwidth of about 100 nm for a typical dye molecule with a red tail which may extend the bandwidth out as much as another 100 nm. It should be noted that the bandwidths referred to are determined from measurement of the full width of the emissions at half peak height (FWHM), and are appropriate in the range of 200 nm to 2000 nm.

By use of the term "a broad wavelength band," with regard to the excitation of the semiconductor nanocrystal is meant absorption of radiation having a wavelength equal to, or shorter than, the wavelength of the onset radiation (the onset radiation is understood to be the longest wavelength (lowest energy) radiation capable of being absorbed by the semiconductor nanocrystal). This onset occurs near to, but at slightly higher energy than the "narrow wavelength band" of the emission. This is in contrast to the "narrow absorption band" of dye molecules which occurs near the emission peak on the high energy side, but drops off rapidly away from that wavelength and is often negligible at wavelengths further than 100 nm from the emission.

The term "barcode" as used herein refers to one or more sizes, size distributions, compositions, or any combination thereof, of semiconductor nanocrystals. Each size, size distribution and/or composition of semiconductor nanocrystals has a characteristic emission spectrum, e.g., wavelength, intensity, FWHM, and/or fluorescent lifetime. In addition to the ability to tune the emission energy by controlling the size of the particular semiconductor nanocrystal, the intensities of that particular emission observed at a specific wavelength are also capable of being varied, thus increasing the potential information density provided by the semiconductor nanocrystal barcode system. In preferred embodiments, 2-15 different intensities may be achieved for a particular emission at a desired wavelength, however, one of ordinary skill in the art will realize that more than fifteen different intensities may be achieved, depending upon the particular application of interest. For the purposes of the present invention, different intensities may be achieved by varying the concentrations of the particular size semiconductor nanocrystal attached to, embedded within or associated with an item, compound or matter of interest. The "barcode" enables the determination of the location or identity of a particular item, compound or matter of interest. For example, semiconductor nanocrystals can be used to barcode pharmaceutical products, blood samples, donated blood, combinatorial libraries including organic compounds, nucleic acids, proteins, peptides, sugars, lipids or a combination of any one or more of these.

By the term "doped metal oxide nanocrystals" refers to a metal oxide, and a dopant comprised of one or more rare earth elements. For example, suitable metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. The rare earth element comprises an element selected from the Lanthanide series and includes, but is not limited to, europium (Eu), cerium (Ce), neodymium (Nd), samarium (Sm), terbium (Tb), gadolinium (Gd), holmium (Ho), thulium (Tm), an oxide thereof, and a combination thereof. As known to those skilled in the art, depending on the dopant, an energized doped metal oxide nanocrystal is capable of emitting light of a particular color. For example, the emission color and brightness (e.g., intensity) of a doped metal oxide nanocrystal comprising $Y_2O_3$:Eu may depend on the concentration of Eu; e.g., emission color may shift from yellow to red with increasing Eu concentration. For purposes of illustration only, representative colors which may be provided are listed in Table 1.

TABLE 1

| Fluorescent Color | Dopant |
|---|---|
| blue | thulium |
| blue | cerium |
| yellow-green | terbium |
| green | holmium |
| green | erbium |
| red | europium |
| reddish orange | samarium |
| orange | neodymium |
| yellow | dysprosium |
| white | praseodymium |
| orange-yellow | europium + terbium |
| orange-red | europium + samarium |

Methods for making doped metal oxide nanocrystals are known to include, but are not limited to a sol-gel process (see, e.g., U.S. Pat. No. 5,637,258 herein incorporated by reference), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm.

The formation of semiconductor nanocrystals is described in U.S. Pat. Nos. 5,571,018; 5,505,928; 5,262,357; 5,571,018; and 5,262,357 each of which are hereby specifically incorporated by reference. Moreover, semiconductor nanocrystals are commercially available, for example, from Evident Technologies of Troy, N.Y.

In one embodiment, the nanocrystals are used in a core/shell configuration wherein a first semiconductor nanocrystal forms a core ranging in diameter, for example, from about 20 Angstroms to about 100 Angstroms, with a shell of another semiconductor nanocrystal material grown over the core nanocrystal to a thickness of, for example, 1-10 monolayers in thickness. When, for example, a 1-10 monolayer thick shell of CdS or ZnS is epitaxially grown over a core of CdSe, there is a dramatic increase in the room temperature photoluminescence quantum yield. Formation of such core/shell nanocrystals is described more fully in a publication entitled "Epitaxial Growth of Highly Luminescent CdSe/CdS Core/Shell Nanocrystals with Photostability and Electronic Accessibility," by Peng et al., published in the Journal of the American Chemical Society, Volume 119, Nov. 30, 1997, at pages 7019-7029, the subject matter of which is hereby specifically incorporated herein by reference.

The semiconductor nanocrystals used in the invention will have the capability of absorbing radiation over a broad wavelength band. This wavelength band includes the range from gamma radiation to microwave radiation. In addition, these semiconductor nanocrystals will have a capability of emitting radiation within a narrow wavelength band of about 40 nm or less, preferably about 20 nm or less, thus permitting the simultaneous use of a plurality of differently colored semiconductor nanocrystal probes with different semiconductor nanocrystals without overlap (or with a small amount of overlap) in wavelengths of emitted light when exposed to the same energy source. Both the absorption and emission properties of semiconductor nanocrystals may serve as advantages over dye molecules which have narrow wavelength bands of absorption (e.g. about 30-50 nm) and broad wavelength bands of emission (e.g. about 100 nm) and broad tails of emission (e.g. another 100 nm) on the red side of the spectrum. Both of these properties of dyes impair the ability to use a plurality of differently colored dyes when exposed to the same energy source.

Furthermore, the frequency or wavelength of the narrow wavelength band of light emitted from the semiconductor nanocrystal may be further selected according to the physical properties, such as size, of the semiconductor nanocrystal. The wavelength band of light emitted by the semiconductor nanocrystal, formed using the above embodiment, may be determined by either (1) the size of the core, or (2) the size of the core and the size of the shell, depending on the composition of the core and shell of the semiconductor nanocrystal. For example, a nanocrystal composed of a 3 nm diameter core of CdSe and a 2 nm thick shell of CdS will emit a narrow wavelength band of light with a peak intensity wavelength of 600 nm. In contrast, a nanocrystal composed of a 3 nm core of CdSe and a 2 nm thick shell of ZnS will emit a narrow wavelength band of light with a peak intensity wavelength of 560 nm. The preparation of monodisperse CdSe quantum dots has been described in detail in Murray et al. (J. Am. Chem. Soc., 115:8706 (1993)), which is hereby incorporated in its entirety by reference.

A plurality of alternatives to changing the size of the semiconductor nanocrystals in order to selectably manipulate the emission wavelength of semiconductor nanocrystals exist. These alternatives include: (1) varying the composition of the nanocrystal, and (2) adding a plurality of shells around the core of the nanocrystal in the form of concentric shells. It should be noted that different wavelengths can also be obtained in multiple shell type semiconductor nanocrystals by respectively using different semiconductor nanocrystals in different shells, i.e., by not using the same semiconductor nanocrystal in each of the plurality of concentric shells.

The emission wavelength of the semiconductor nanocrystal may be varied by tailoring the composition, or alloy, of the semiconductor nanocrystal. As an illustration, a CdS semiconductor nanocrystal, having an emission wavelength of 400 nm, may be alloyed with a CdSe semiconductor nanocrystal, having an emission wavelength of 530 nm. When a nanocrystal is prepared using an alloy of CdS and CdSe, the wavelength of the emission from a plurality of identically sized nanocrystals may be tuned continuously from 400 nm to 530 nm depending on the ratio of S to Se present in the nanocrystal. The ability to select from different emission wavelengths while maintaining the same size of the semiconductor nanocrystal may be important in applications which require the semiconductor nanocrystals to be uniform in size, or for example, an application which requires all semiconductor nanocrystals to have very small dimensions.

Techniques for producing semiconductor nanocrystals that fluoresce in a narrow spectral distribution of a selected color are discussed in, for example, Dabbousi et al. (1997) J. Phys. Chem. B 101:9463-9475 and U.S. Pat. No. 6,322,901 which are herein incorporated by reference. For example, CdSe nanocrystals can be produced that emit light visible to the human eye, so that in combination with a source of higher energy than the highest energy of the desired color, these nanocrystals can be tailored to produce visible light of any spectral distribution. Semiconductor nanocrystals can also be produced that emit in the ultraviolet and infra red spectral ranges. Examples of ultraviolet- and infra red-emitting nanocrystals are, e.g., CdS, ZnS and ZnSe, and InAs, CdTe and MgTe, respectively. The color of light produced by a particular size, size distribution and/or composition of a semiconductor nanocrystal may be readily calculated or measured by methods which will be apparent to those skilled in the art. As an example of these measurement techniques, the band gaps for nanocrystals of CdSe of sizes ranging from 12 Angstroms to 115 Angstroms are given in Murray et al. J. Am. Chem. Soc. 115:8706 (1993). These techniques allow ready calculation of an appropriate size, size distribution and/or composition of semiconductor nanocrystals and choice of excitation light source to produce a nanocrystal capable of emitting light device of any desired wavelength.

Dabbousi et al. also discloses a method that can be used for overcoating nanocrystals composed of CdS, CdSe, or CdTe with ZnS, ZnSe, or mixtures thereof. Before overcoating, a nanocrystal core is prepared by a method described in Murray et al. that yields a substantially monodisperse size distribution. These methods can be used to prepare separate populations of semiconductor nanocrystals, wherein each population exhibits a different characteristic photoluminescence spectrum.

The present invention provides a method for determining and/or quantifying the movement of a fluid from one container to another. The methods of the present invention, by way of example, can (1) detect the presence and amounts of reagent transferred into a reactor vessel, e.g., verifying the addition of appropriate amounts of a reactant into a reaction vessel to form a chemical product; (2) localize a chemical compound, e.g., determination of whether and how much of an addition product is present in a subsequent processing step or product, such as for use in high volume screening of nucleic acid testing or in blood testing; (3) detect the removal of fluid from a container, e.g., verifying or quantifying the cleaning of a fermentor or bioreactor and determining the presence, identity, and quantity of residual elements; (4) quantify the dilution of a composition, e.g., verifying that a primary standard solution has been diluted to a predetermined concentration; (5) monitor liquid transport, e.g., monitoring liquid transport in hydraulic systems; (6) evaluate and verify microfluidic dilutions, volume samplings, and other critical fluidic manipulations; and/or (7) monitor and quantify the amounts of solid materials that are dissolved in a fluid.

The method of the present invention includes adding a fluorescent semiconductor nanocrystal having a defined characteristic spectral emission based on the physical properties of the semiconductor nanocrystal, which is tunable to a desired energy by selection of the particle size, size distribution and composition of the semiconductor nanocrystal, to a first fluid composition. When the first fluid composition containing the semiconductor nanocrystal is transferred to a second fluid composition, the presence and amount of the semiconductor nanocrystal, and therefore the presence and amount of the first fluid in the second fluid, can be detected by optically monitoring the emission of the semiconductor nanocrystal and determining the relative fluorescence as is understood in the art.

In one embodiment of the present invention, semiconductor nanocrystals may be added to a first fluid composition. To measure, determine, and quantify the presence and amount of the first fluid in a second fluid composition when the first fluid composition has been transferred into the second fluid composition, the semiconductor nanocrystal present in the second composition, by virtue of the transfer of the first composition into the second composition, may be spectroscopically viewed or otherwise detected, for example, by irradiation of the composition with an excitation light source to determine the presence and quantity of the first composition in the second composition.

Since the semiconductor nanocrystal emits a characteristic emission spectrum based on the selection of the particle size, size distribution and composition of the semiconductor nanocrystal which can be observed and measured, the quantity of the first composition transferred into the second composition can be determined. For example, by knowing the amount of semiconductor nanocrystal in the first solution, true volume verification of the liquid transfer can be determined by analyzing the existence and amount of the semiconductor nanocrystals, which were originally present in the first composition, in the second composition. Likewise, the extent of fluid transfer can be determined by quantifying the ratio of semiconductor nanocrystals present in the second composition to the semiconductor nanocrystals present in the first composition.

For example, if a first composition contains 100 semiconductor nanocrystals/ml and 2.5 ml of the first composition is transferred into a second fluid composition, the transfer of the first fluid can be detected by the presence of the homogeneously distributed semiconductor nanocrystals whereas the quantity of the first fluid delivered into the second fluid can be verified by measuring the amount of semiconductor nanocrystals in the second composition. In this example, if the second composition contains 245 semiconductor nanocrystals it can be quantified that 2.45 ml of the first composition (or 98%) was delivered to the second composition. This method has particular application in, for example, high volume nucleic acid screening assays as a technique to verify reaction delivery. One of the attributes of the semiconductor nanocrystals is that they can be constructed to luminescence in regions of the spectrum outside the normal visible range, in particular, the near infrared region of the electromagnetic spectrum. This allows for the use of the semiconductor nanocrystals as tracers in opaque solutions in the visible region of the spectrum. An example of such a solution is whole blood. Others examples include bioreactor media, disrupted mixtures of cells, and other liquid media opaque to visual inspection.

Nucleic acid testing ("NAT") detects very small amounts of genetic material by copying the target nucleic acid numerous times, resulting in, for example, a billion-fold amplification of the target. For example, NAT can detect ribonucleic acid (RNA) from HIV-1 and HCV when tested in pools of 16 biological samples obtained from multiple donors. It can also be used to test biological samples from individuals and label and identify DNA, RNA and nucleotides. In quantitative applications of repetitive amplifications technologies such as PCR, the amplification outcomes are dependent upon the initial conditions. Therefore, verifying the actual concentration of a nucleic acid component relative to previous concentration conditions in a time synchronous or non-synchronous replicate prior to amplification can have significant implications on assay reproducibility. The use of the semiconductor nanocrystals provides a useful way improve the certainty of concentrations and therefore the precision of the assay.

In an alternative embodiment, the present invention includes adding a fluorescent semiconductor nanocrystal having a defined characteristic spectral emission based on the physical properties of the semiconductor nanocrystal, which is tunable to a desired energy by selection of the particle size, size distribution and composition of the semiconductor nanocrystal, to a first fluid composition having solid materials dissolved therein. Many chemical and biological materials are purified as aqueous solutions or when dissolved in a variety of organic solvents. Through a series of manipulations of these solutions, such as, for example, chromatography, electroporetic separations, elutions, dialysis, and the like, the target component is separated from contaminants and obtained as a purified material in solution. Chemically inert semiconductor nanocrystals can be homogeneously dispersed at a known concentration into the purified solution. After lyophilization, the semiconductor nanocrystals would remain homogeneously dispersed in the solid product and could serve to identify and quantify the amount of solid added to make a subsequent solution. This method is particularly useful for primary standards that are frequently provided as lyophilized materials (for stability reasons) and provides improved precision when preparing initial stock solutions (as well as the subsequent dilutions). Moreover, by specifically labeling a component to be purified in the crude state with semiconductor nanocrystals (in such a way as to not interfere with the chemical or biological activity), it is possible to track the increasing purity of the material as it is taken through the various purification manipulations.

In an alternative embodiment, the measurement, determination and quantification of the presence and amount of the first fluid in a second fluid composition may be determined by taking a unit sample of the second composition and spectroscopically viewing or otherwise detecting, for example, by irradiation of the unit sample with an excitation light source to determine the presence and quantity of the semiconductor nanocrystal in the unit sample.

In yet another embodiment of the present invention, it is possible to measure, determine and quantify the presence and amount of a plurality of sequentially or batch added fluids in a final fluid composition when the plurality of fluid compositions include different semiconductor nanocrystals based on a selection of the particle size, size distribution and composition of the semiconductor nanocrystal. Thus, for example, a first composition to be added to the final composition may include semiconductor nanocrystals which emit a first emission spectrum which is either spectroscopically viewed or otherwise detected, for example, by irradiation of the composition with an excitation light source. A second composition to be added to the final composition may include semiconductor nanocrystals which emit a second emission spectrum based on the particle size, size distribution and composition of the semiconductor nanocrystal. A third composition to be added to the final composition may include semiconductor nanocrystals which emit a third emission spectrum, and the like. The quantity of the first, second, third, etc. compositions transferred into the final composition can be determined by analyzing the existence and amount of the respective semiconductor nanocrystals in the final composition which were originally present in the first, second, third, etc. compositions. Likewise, the extent of fluid transfer from the plurality of compositions into the final composition can be determined by quantifying the ratio of semiconductor nanocrystals present in the final composition to the semiconductor nanocrystals present in the plurality of compositions. The emission spectra of a population of semiconductor nanocrystals have linewidths as narrow as 25-30 nm. The combination of tunability, narrow linewidths, and symmetric emission spectra without a tailing region provides for high resolution of multiply-sized nanocrystals, e.g., populations of monodisperse semiconductor nanocrystals having multiple distinct size distributions.

In the alternative, the quantity of the first, second, third, etc. compositions transferred into the final composition can be determined by analyzing the existence and amount of the respective semiconductor nanocrystals in a unit sample taken from the final composition.

In another alternative embodiment, the semiconductor nanocrystal contains a linking agent that is introduced into an environment containing a chemical/biological target to be marked whereby the semiconductor nanocrystal is linked with the target by the linking agent. Linking semiconductor nanocrystals to chemical or biological targets is known in the art as illustrated by, for example, U.S. Pat. Nos. 5,990,479; 6,207,392; 6,114,038; 6,221,602; and 6,235,540, which are herein incorporated by reference. After the composition is transferred to a subsequent composition, the semiconductor nanocrystal:target complex may be spectroscopically viewed or otherwise detected, for example, by irradiation of the complex with an excitation light source to determine the presence of the chemical/biological target. Since the semiconductor nanocrystal emits a characteristic emission spectrum which can be observed and measured, the quantity of the chemical/biological target transferred can be determined. For example, by knowing the amount of semiconductor nanocrystal in the first solution, the true volume verification of the liquid transfer can be determined by verifying that the semiconductor nanocrystals present in the first composition are present, in their entirety, in the second composition. Likewise, the extent of fluid transfer can be determined by quantifying the ratio of semiconductor nanocrystals present in the second composition to the semiconductor nanocrystals present in the first composition.

The present invention is also directed to monitoring fluid transport. Fluid transport can be measured in a batch or continuous process by sampling the fluid flow and measuring the amount of semiconductor nanocrystals present in the unit sample. This method has particular application in, for example, the monitoring of liquid transport in hydraulic systems, and evaluation and verification of microfluidic dilutions, volume samplings and other critical fluidic manipulations.

In another embodiment of the present invention, the semiconductor nanocrystals are used to evaluate and verify microfluidic dilutions, volume samplings, and other critical fluidic manipulations. In microfluidic systems acts of valving, fluid diversion and sampling are most commonly done by changing the pumping rate, charge gating and fluid intersections, or by intermittent or continuous manual modifications of fluid routes. Currently there is no way to verify that those commands to the liquid system elements have been executed properly. Adding a semiconductor nanocrystal to a microfluidic system would allow for the precise evaluation and verification of microfluidic dilutions, volume samplings, and other critical fluidic manipulations.

In another embodiment of the present invention, the semiconductor nanocrystals are used to determine and quantify the dilution of a first composition. By adding a semiconductor nanocrystal to a first solution exact dilutions of the solution can be prepared by measuring and quantifying the presence in the diluted composition of the semiconductor nanocrystals. For example, if a first solution contains 100 semiconductor nanocrystals homogeneously dispersed per unit volume the solution can be diluted by exact standards by measuring the semiconductor nanocrystals in the diluted composition. Thus, by example, a solution containing ten semiconductor nanocrystals has been diluted ten-fold. Due to the sensitivity of the semiconductor nanocrystals, diluted solutions can be made which can be diluted to the order of 1,000 to 100,000, depending on the beginning concentration of semiconductor nanocrystals. This method has particular application in, for example, the preparation of primary standards in which exact, traceable volume additions are required.

In another embodiment of the present invention, semiconductor nanocrystals are added to a container, such as a reaction vessel, during a phase of the reaction. Once the reaction product is obtained, the reaction vessel is cleaned during a first cleaning iteration. Following the first cleaning iteration, the reactor vessel is spectroscopically viewed or otherwise irradiated with an excitation light source to determine the presence and quantity of the semiconductor nanocrystal present in the reactor vessel. The presence and amount of the semiconductor nanocrystals provides information on the degree to which the reactor vessel has been cleaned. The reactor vessel can thereafter undergo further cleaning iterations, with subsequent detection and quantification of the semiconductor nanocrystals, until the reactor vessel is cleaned to a specified degree. This method has particular application in, fermentation and bioreactor.

The determination of the degree of cleanliness of the reactor enables verification of the degree of residual components removed. Moreover, allowing quantification of the degree of cleanliness of a reactor would enable a single reactor to be used for a variety of reaction products. This is especially important in the production of pharmaceuticals and biomolecular products where the cost of separate production facilities can be prohibitive. In addition, being able to use the same reactor for several different pharmaceutical or biomolecular products would enable a reactor to be used for different pharmaceutical or biomolecular products, depending upon the needs of patients for a particular pharmaceutical or the application requirements for a particular biomolecular product.

Luminescent semiconductor nanocrystals are useful at low concentrations of fluids when mixed with larger volume solutions. Luminescent semiconductor nanocrystals can track the addition of small volumes of material into large volumes of diluent where the differences between the luminescent semiconductor nanocrystal and the diluent could be as large as one part in one million or higher. Similarly, remainders of solutions as small as one nanoliter from one mL could be detected by the use of semiconductor nanocrystals. The use of luminescent semiconductor nanocrystals in volumes as small as 1-10 nL added to 1.0 mL could be confirmed. Moreover, due to the lack of self quenching by luminescent semiconductor nanocrystals, concentrations up to 20 uM could be employed which would give a dilution linear range of 9 logs. This would mean that a 1 pL addition or remnant could be quantified in a 1 mL total volume. Self quenching and the innately nonlinear response would limit the utility of typical chemical fluorophores The following Examples serve to illustrate the invention. The Examples should not be construed to limit the present invention, but instead serve to illustrate preferred embodiments thereof.

Figure 1:
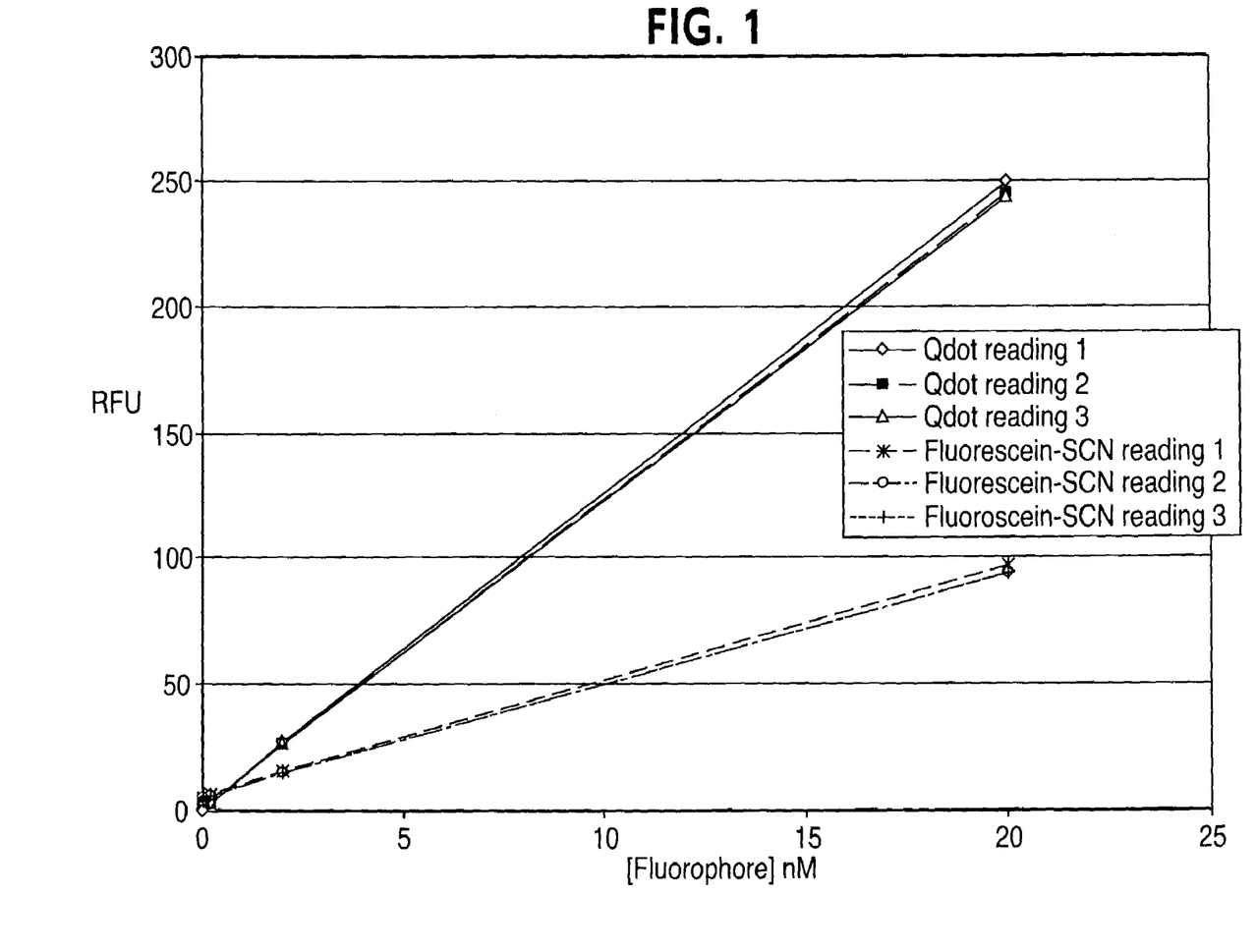
FIG. 1 is a graph of the relative fluorescence versus concentration of luminescent semiconductor nanocrystals and a typical fluorophore.

A dilution analysis was performed to evaluate the optical properties of luminescent semiconductor nanocrystals relative to a standard fluorophore, fluorescein isothiocyanate. Luminescent semiconductor nanocrystals, 655 Q-Dot commercially available from Quantum Dot Corporation of Hayward, Calif. with an emission maximum of 655 nm, were stimulated to fluoresce by light at approximately 450 nm. The fluorescein isothiocyanate emitted light at approximately 405 nm when stimulated at 395 nM. A solution of luminescent semiconductor nanocrystals and fluorophore were both adjusted to a concentration of 20 nM and diluted serially through six logs. The emission of both the luminescent semiconductor nanocrystals and the fluorescein isothiocyanate were observed and quantified. As can be seen from FIG. 1, the luminescent semiconductor nanocrystals provided a significantly more linear response through this dilution sequence than the standard fluorophor, fluorescein isothiocyanate. This is shown by the dilution sequence over 6 logs, intercepting at zero. Three separate tests were run. As can also be seen from FIG. 1, the luminescent semiconductor nanocrystals are approximately 2.5 times more brilliant than the typical fluorophore, fluorescein isothiocyanate.

While the invention has been described with reference to particularly preferred embodiments, it will be appreciated that modifications can be made without departing from the spirit of the invention. Such modifications are intended to fall within the scope of the appended claims.

What is claimed is:

1. A method comprising:
   providing a first composition having a first fluid therein;
   providing a second composition having a second fluid therein, wherein said second composition includes a predetermined amount of luminescent semiconductor nanocrystals capable of emitting electromagnetic radiation in a narrow wavelength band when excited;
   transferring all or a portion of said second composition into said first composition to form a third composition;
   exposing said third composition to energy capable of exciting said luminescent semiconductor nanocrystals;
   detecting the electromagnetic radiation emitted from said luminescent semiconductor nanocrystals in said third composition; and
   quantifying the luminescent semiconductor nanocrvstals in said third composition to verify the volume of said second composition into said first composition to form said third composition.

2. The method according to claim 1, wherein said semiconductor nanocrystal is a core/shell nanocrystal.

3. The method according to claim 1, wherein said semiconductor nanocrystal has a diameter between about 2 nm and about 50 nm.

4. The method according to claim 3, wherein said semiconductor nanocrystal has a diameter between about 2 nm and about 20 nm.

5. The method according to claim 1, wherein said semiconductor nanocrystal is selected from the group consisting of ZnS, ZnSe, ZnTe, CdS, CdSe, CdTe, HgS, HgSe, HgTe, MgS, MgSe, MgTe, CaS, CaSe, GaTe, SrS, SrSe, SrTe, BaS, BaSe, BaTe, and mixtures thereof.

6. The method according to claim 2, wherein said semiconductor nanocrystal has a core which comprises CdS.

7. The method according to claim 6, wherein said semiconductor nanocrystal has a shell which comprises CdS.

8. The method according to claim 6, wherein said semiconductor nanocrystal has a shell which comprises ZnS.

9. The method according to claim 1, wherein said semiconductor nanocrystals are monodisperse.

10. The method according to claim 2, wherein said semiconductor nanocrystal has a core diameter between about 2 nm and about 50 nm.

11. The method according to claim 2, wherein said semiconductor nanocrystal has a core diameter between about 2 mn and about 6 mm.

12. The method according to claim 10, wherein said semiconductor nanocrystal includes a shell having a thickness of about 2 nm.

13. The method according to claim 11, wherein said semiconductor nanocrystal includes a shell having a thickness of about 2 nm.

14. The method according to claim 1, wherein said second fluid comprises a target and said semiconductor nanocrystal is linked to the target.

15. The method according to claim 1, wherein said method is used in nucleic acid testing.

16. The method according to claim 1, wherein the luminescent semiconductor nanocrystals are present in the second composition in an amount from about 0.0002 nanomolar to about 20 nanomolar.

* * * * *